(12) United States Patent
Ishii et al.

(10) Patent No.: US 6,205,863 B1
(45) Date of Patent: Mar. 27, 2001

(54) MATERIAL TESTING MACHINE HAVING A CONTROL SYSTEM FOR FEEDBACK-CONTROLLING THE OPERATION OF A SERVO SYSTEM

(75) Inventors: Yuzo Ishii; Masayuki Matsumoto; Nobunari Takahashi, all of Toyohashi; Susumu Kamio; Katsumi Yamashita, both of Kitakyushu, all of (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/133,838

(22) Filed: Aug. 13, 1998

(30) Foreign Application Priority Data

Aug. 13, 1997 (JP) .................................................... 9-218547
Aug. 13, 1997 (JP) .................................................... 9-218548
Aug. 13, 1997 (JP) .................................................... 9-218549

(51) Int. Cl.[7] ...................................................... G01N 3/00
(52) U.S. Cl. .............................................. 73/805; 73/806
(58) Field of Search ............................. 73/788, 790, 797, 73/798, 805, 806, 807, 808, 804, 837

(56) References Cited

U.S. PATENT DOCUMENTS

| 3,664,179 | * | 5/1972 | Danko et al. | 73/579 |
|---|---|---|---|---|
| 4,171,644 | * | 10/1979 | Beller | 73/631 |
| 4,235,114 | | 11/1980 | Mohler . | |
| 4,802,367 | | 2/1989 | Petersen et al. . | |
| 5,511,431 | * | 4/1996 | Hinton | 73/806 |

FOREIGN PATENT DOCUMENTS 2205959A  12/1988  (GB) .

OTHER PUBLICATIONS

Patent Abstracts of Japan, JP 09 203700 A, Dec. 25, 1997, vol. 1997, No. 12.
Patent Abstracts of Japan, JP 03 448033 A, Jan. 31, 1992, vol. 016, No. 042.

* cited by examiner

Primary Examiner—Max Noori
(74) Attorney, Agent, or Firm—Birch, Stewart, Kolasch & Birch, LLP

(57) ABSTRACT

A material testing machine includes a control system for feedback-controlling the operation of a servo system, including an actuator for applying a load to a test piece, during material testing. Prior to the material testing, the stiffness of the test piece is estimated on the basis of the actual load and displacement which are detected after the displacement of the test piece is stabilized while maintaining the load observed when a minute displacement is generated in the test piece as the control gain is increased from its minimum value. In accordance with the estimated stiffness, the initial value of the control gain for the control system is set. During the material testing, the control gain is corrected in accordance with the stiffness of the test piece estimated based on the actual load and displacement of the test piece. Upon changeover between the force control mode and the displacement control mode, the initial setting of the control output value for post-changeover is made based on the control output value given to the servo system just before the changeover, to thereby achieve a smooth control mode changeover.

5 Claims, 11 Drawing Sheets

FIG. 7
| CONTROL SYSTEM | ELASTIC CONSTANT | $KL_1$ | $KL_2$ | ~ | $KL_N$ |
|---|---|---|---|---|---|
| FORCE | PROPORTIONAL | $KP_1$ | $KP_2$ | ~ | $KP_N$ |
|  | INTEGRAL | $KI_1$ | $KI_2$ |  | $KI_N$ |
| DISPLACEMENT | PROPORTIONAL | $KP_1$ | $KP_2$ | ~ | $KP_N$ |
|  | INTEGRAL | $KI_1$ | $KI_2$ |  | $KI_N$ |
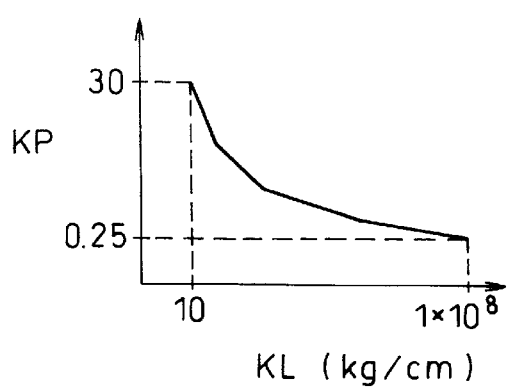
FIG. 8
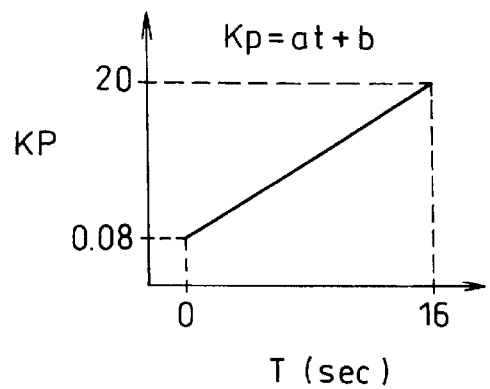
FIG. 9

F I G. 10
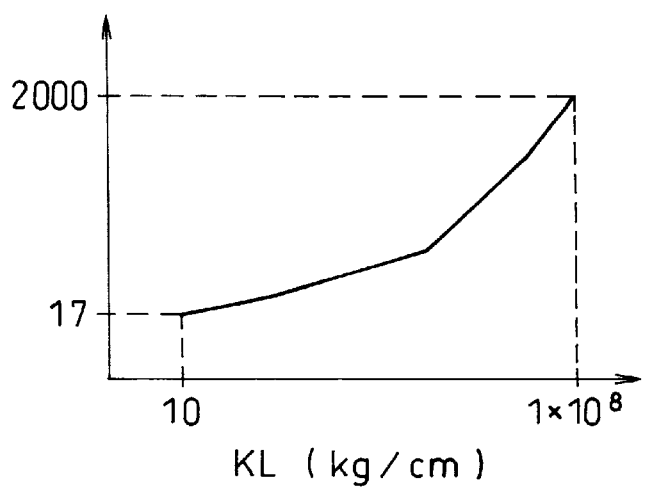
F I G. 11
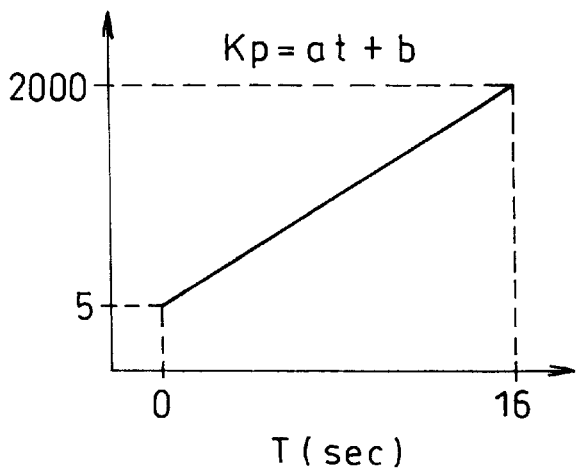
F I G. 12
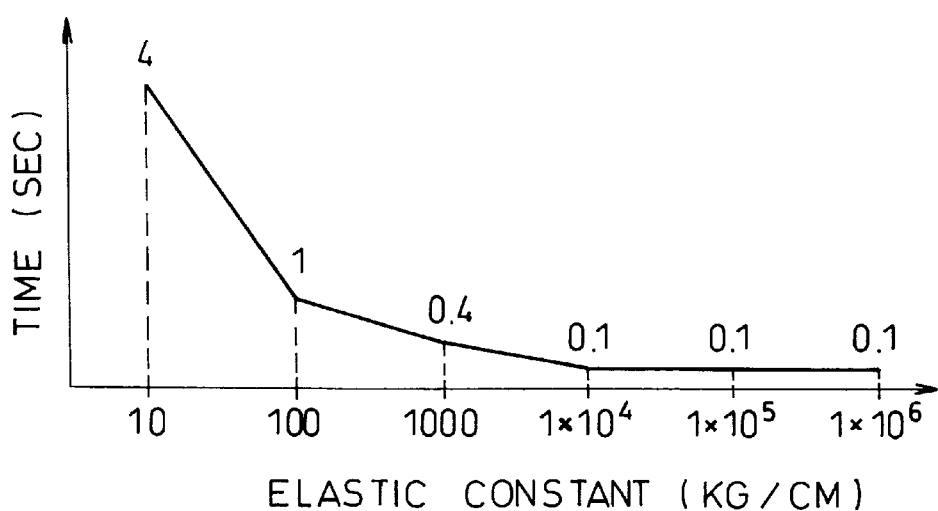

MATERIAL TESTING MACHINE HAVING A CONTROL SYSTEM FOR FEEDBACK-CONTROLLING THE OPERATION OF A SERVO SYSTEM

BACKGROUND OF THE INVENTION

1. Technical Field

The present invention relates to a material testing machine, and more particularly, to an electrohydraulic servo-controlled material testing machine.

2. Related Art

An electrohydraulic servo-controlled material testing machine is known which is comprised of a controller for supplying, via a servo amplifier, an electric signal input to an electrohydraulic servo valve provided between a hydraulic power source and a hydraulic actuator such as a hydraulic cylinder, the electric signal input varying in accordance with a target displacement of a movable part of the actuator. Typically, the quantity of fluid output from the servo valve varies in response to the electric signal input, and the movable part of the hydraulic cylinder is displaced at a speed proportional to the fluid quantity, whereby a load is applied to a test piece held between the cylinder movable part and a main body of the testing machine. An actual displacement of the cylinder movable part is detected and is supplied as a feedback signal to the controller. Under the control of the controller, a feedback control is carried out to cause the actual displacement to close to a target displacement.

In this specification, the term "displacement of a test piece" indicates the displacement of one end of the test piece coupled to a movable part of an actuator which is caused by the displacement of the movable part of the actuator. In a material testing machine of a type provided with two actuators whose movable parts hold a test piece therebetween and are typically displaced in opposite directions, the term "displacement of the test piece" indicates the sum of displacements of opposite ends of the test piece caused by the displacement of the two movable arts of the actuators. That is, the term "displacement of the test piece" indicates deformation of the test piece caused by the isplacement of the movable part(s) of the actuator.

The term "servo system" indicates a system mainly comprised of an actuator, a servo amplifier, and a servo valve. The term "control system" indicates a system mainly comprised of a servo system and a controller for controlling the operation of the servo system. The term "control loop" or "feedback control loop" indicates a loop mainly comprised of a servo system, a controller, and a test piece. Moreover, the term "force control system" indicates a control system for carrying out a feedback control with use of an actual force applied to the test piece, as the controlled variable, whereas the term "displacement control system" indicates a system for executing a feedback control using, as a controlled variable, an actual displacement of the test piece. The term "load" indicates a broadly defined load which includes a force applied to the test piece and generally referred to as a load, and which also includes the displacement of the test piece. In case that the actual load or the actual displacement is referred to as a controlled variable, the term "control objective value" or "control target value" indicates a target load.

A typical electrohydraulic servo-controlled material testing machine performs material testing, while controlling the actual load given to the test piece (the actual force applied to or the actual displacement of the test piece) to the target load in a feedback manner. Thus, it is preferable to optimize the control gain for the feedback control, thereby performing the material testing efficiently and stably because the control response lowers so that much time is required for material testing if the control gain is excessively small, whereas hunting phenomenon occurs so that the stability and reliability of the testing are impaired, sometimes leading to test piece breakage if the control gain is excessively large.

The optimum control gain for the feedback control varies depending on mechanical properties, especially stiffness (elastic constant), of the test piece. For this reason, in the case of material testing as for a test piece whose stiffness is unknown, preliminary testing is heretofore carried out repeatedly while changing the control gain, to thereby determine the optimum control gain in a trial and error manner. This requires labor and time.

Moreover, the stiffness of the test piece varies in dependence on the load given to the test piece. Especially, the stiffness largely varies if the test piece is in its elastic deformation region. In other words, the optimum control gain for feedback control may change as the stiffness changes, even in the course of material testing, causing the feedback control to be improper so that the testing efficiency and stability may be impaired.

An electrohydraulic servo-controlled material testing machine may be of a type having a force control system for feedback-controlling the actual force applied to the test piece to the target force and a displacement control system for feedback-controlling the actual displacement of the test piece to the target displacement, and adapted to select a desired one of these control systems to carry out the feedback control in a force control mode or a displacement control mode. Generally, either one of the control modes is selected during the testing in accordance with instructions given by an operator.

In a testing machine of a type having a controller for controlling the operation of the servo system, the control gain for the control loop which is comprised of the servo system, the controller, and the test piece, especially the control gain for the controller largely differs according to whether the testing machine operates in the force control mode or in the displacement control mode. That is, the control gain for the controller is set to be small in the force control mode, whereas it is set to be large in the displacement control mode. Moreover, the mechanical properties, especially the stiffness of the test piece generally varies in dependence on the load given to the test piece, and the proper control gain greatly changes depending on the mechanical properties of the test piece. If the force control mode is changed over to the displacement control mode in a condition where the load is kept applied, the applied load abruptly changes attributable to the difference of control gain between the two control modes, so that a large shock may be applied to the test piece.

Upon changeover of the control mode, heretofore, the operation of the servo system is temporarily stopped to release the load given to the test piece, and the servo system is operated in the control mode after the changeover. The material testing is interrupted each time the control mode is changed over, so that the testing efficiency lowers, and efforts to release the load are troublesome.

SUMMARY OF THE INVENTION

An object of the present invention is to provide a material testing machine capable of always optimizing the control gain for feedback control even if mechanical properties of a test piece vary during material testing, to thereby carry out material testing with accuracy in a stable manner.

Another object of the present invention is to provide a material testing machine capable of efficiently easily optimizing a feedback control gain for material testing in advance prior to execution of material testing, even in respect of a test piece whose mechanical properties are unknown, without applying excessive load to the test piece, thereby improving the efficiency of material testing.

A further object of the present invention is to provide a material testing machine capable of making a smooth changeover between a force control mode and a displacement control mode without applying excessive load to a test piece, to prevent the test piece from being applied with a shock.

According to a first aspect of the present invention, there is provided a material testing machine for measuring a mechanical property of a test piece based on a load given to the test piece and a mechanical change (e.g., displacement or distortion) generated in the test piece, while feedback-controlling an operation of a servo system including a hydraulic actuator which gives the load to the test piece by means of a controller such that actual load applied to the test piece coincides with target load.

The material testing machine comprises: gain setting means for setting the control gain for the feedback control performed during material testing; estimating means for estimating a mechanical property of the test piece based on an actual load and a mechanical change in the test piece which are periodically detected during the material testing performed while carrying out the feedback control; and gain correcting means for correcting the control gain set by the gain setting means in accordance with the estimated mechanical property.

With this testing machine, the control gain for the feedback control is corrected based on the mechanical property of the test piece estimated on the basis of the load and the mechanical change (e.g., displacement or distortion) in the test piece, periodically detected during the material testing. If the control gain set by the gain setting means is deviated from an optimum value or if the control gain is deviated from the optimum value as the mechanical change occurs in the test piece during the material testing, the control gain is corrected to be optimized. Thus, the material testing can be made stably with high accuracy, while always giving a proper load to the test piece.

Preferably, the estimating means estimates stiffness of the test piece based on the actual load and the actual displacement of the test piece which are periodically detected during the material testing.

With this preferred arrangement, an optimum control gain can be attained by correcting the control gain based on the result of estimation in respect of the stiffness of the test piece which especially affects on the control gain.

Preferably, prior to the material testing, initial setting is made to set the initial value of the control gain for the feedback control performed during the material testing. In the initial setting, a load is given to the test piece while performing a feedback control similar to the feedback control performed during the material testing. Further, the actual load of and the mechanical change in the test piece are detected, and the mechanical property of the test piece is estimated. During the initial setting, the gain setting means causes the control gain to gradually increase from the minimum value of the control gain. The gain correcting means corrects the control gain to thereby set the initial value of the control gain, based on the estimated mechanical property of the test piece. The estimated mechanical property is determined by the estimating means based on the actual load applied to and the mechanical change generated in the test piece which are observed when a mechanical change in the test piece is detected during the initial setting. The material testing is started after the initial value of the control gain is set.

With this preferred arrangement, the material testing can be started after the initial value of the control gain for the control system is properly set, and hence the material testing can be carried out without applying an undesired excessive load to the test piece.

Preferably, the gain correcting means corrects the control gain set by the gain setting means to coincide with the control gain which corresponds to the estimated mechanical property determined by the estimating means, by searching a table in which the control gain for every type of test piece is set in advance as a function of a mechanical property of the test piece.

With this preferred arrangement, by referring to the table showing the relationship between the mechanical property of test piece and an optimum control gain acquired beforehand for every type of test pieces, an optimum control gain for the feedback control to be performed during the material testing can be set in advance, thereby easily efficiently stabilizing the operation of the servo system during the material testing. Thus, the material testing can be carried out with accuracy in a stabilized manner.

According to a second aspect of the present invention, a material testing machine has the same basic construction as that of the testing machine according to the first aspect of the present invention. The same is applied to material testing machines according to a third aspect of the present invention.

The material testing machine according to the second aspect of the present invention comprises: load maintaining means for maintaining load observed at a time when a minute change in the test piece (e.g., a minute change in actual load given to the test piece or a minute mechanical change in the test piece) is detected while applying a gradually increasing load prior to material testing; estimating means for estimating a mechanical property of the test piece based on actual load and a mechanical change of the test piece respectively detected after a displacement of the test piece is stabilized while the load observed when the minute change in the test piece was detected is maintained; and initial gain setting means for setting an initial value of the control gain for the feedback control in accordance with the estimated mechanical property of the test piece.

With this testing machine, even if a mechanical property (e.g., stiffness) of a test piece is unknown, the mechanical property of the test piece can be accurately estimated within a short period of time, without giving an undesired load to the test piece. Further, the initial value of the control gain suited to the estimated mechanical property can be automatically set. Thus, material testing can be made efficiently with ease in respect of various test pieces including ones whose mechanical property is unknown.

Preferably, the initial gain setting means sets an initial value of a control gain for the controller in accordance with the estimated mechanical property of the test piece determined by the estimating means.

With this preferred testing machine, the initial value of the control gain for the feedback control (or for a control loop including the servo system, the controller, and the test piece) can be properly set with ease.

Preferably, the initial setting means sets the control gain at a minimum value of the control gain when giving of the load to the test piece is started prior to material testing, and thereafter the control gain is gradually increased with elapse of time. The minute change in the test piece is detected when a mechanical change in the test piece beyond detecting resolution of a detector is detected.

With this preferred arrangement, excessive load can be prevented from being applied to the test piece due to improper setting of the initial value of the control gain for the feedback control which is carried out during the material testing.

Preferably, the initial gain setting means searches a table in which the control gain is stored beforehand as a function of the mechanical property of the test piece, to thereby set the initial value of the control gain based on the mechanical property estimated by the estimating means.

With this preferred arrangement, the initial value of the control gain suitable for material testing can be automatically set with use of the relationship between mechanical properties of various test pieces and optimum control gains acquired in advance.

According to a third aspect of the present invention, a material testing machine comprises: a force control system including a controller for feedback-controlling the operation of the servo system based on an actual force applied to the test piece, the actual force serving as a controlled variable in the feedback control; a displacement control system including a controller for feedback-controlling the operation of the servo system based on an actual displacement of the test piece, the actual displacement serving as a controlled variable in the feedback control; and control system changeover means for selectively operating either the force control system or the displacement control system. The control system changeover means makes initial setting of a control output value to be supplied from the controller in the post-changeover control system, based on a control output value supplied from the controller in the pre-changeover control system to the servo system just before the changeover, and then makes the control system changeover.

With this testing machine, by initially setting the control output value from the controller of the post-changeover control system on the basis of the control output value supplied to the servo system just before the control system changeover, a difference between the control gains of both the control systems can be eliminated. As a result, irrespective of the difference between the control gain in the force control system and that in the displacement control system, the control system changeover can be made smoothly, without providing a shock to the test piece and without the need of temporarily releasing the force applied to the test piece.

Preferably, the controller of the force control system determines the control output value $U_K$ to be supplied to the servo system in accordance with a formula given by:

$$U_K = P_K \cdot \Delta e_K + I_K \cdot \Sigma K$$

where $P_K$ and $I_K$ represent a proportional control gain and an integral control gain which are set beforehand, and $\Delta e_K$ and $\Sigma K$ represent an error between a target force and an actual force applied to the test piece and an integral of the error.

The controller of the displacement control system determines the control output value $U_H$ to be supplied to the servo system in accordance with a formula given by:

$$U_H = P_H \cdot \Delta e_H + I_H \cdot \Sigma H$$

where $P_H$ and $I_H$ represent a proportional control gain and an integral control gain which are set beforehand, and $\Delta e_H$ and $\Sigma H$ represent an error between a target displacement and an actual displacement of the test piece and an integral of the error.

Based on the control output value $U_K$ or $U_H$ given to the servo system just before the control system changeover, the control system changeover mean determines the integral $\Sigma H$ or $\Sigma K$ of the error between the controlled variable initially set in the post-changeover control system and a control objective value in accordance with formulas, given by:

$$\Sigma H = (U_K - P_H \cdot \Delta e_H)/I_H$$

$$\Sigma K = (U_H - P_K \cdot \Delta e_K)/I_K$$

to thereby make the control output values $U_K$ and $U_H$ equal to each other, which values are given to the servo system before and after the control system changeover.

With this preferred arrangement, it is possible to cause the control output values $U_K$ and $U_H$ given to the servo system before and after the control system changeover to be equal to each other, whereby the changeover of the control system can be carried out smoothly.

These and other features and advantages will be apparent from a detailed description of particular embodiments of this invention illustrated as non-exclusive examples in the appended drawings.

BRIEF DESCRIPTION OF THE DRAWINGS

FIG. 7 is a view showing a table in which various combinations of elastic constants of test pieces and optimum control gains are shown;

FIG. 8 is a graph showing a relationship between proportional gain and elastic constant of the test piece observed at the time of step response of the force control system;

FIG. 9 is a graph showing an elapsed time vs. proportional gain characteristic for automatic control gain setting processing in respect of the force control system;

FIG. 10 is a graph showing a relationship between proportional gain and elastic constant of the test piece observed at the time of step response of the displacement control system;

FIG. 11 is a graph showing an elapsed time vs. proportional gain characteristic for the automatic control gain setting processing in the displacement control system;

FIG. 12 is a graph showing a time period required for the displacement to be stabilized, at step response, as a function of elastic constant of the test piece;

DETAILED DESCRIPTION

With reference to the appended drawings, an electrohydraulic servo-controlled material testing machine according to an embodiment of the present invention will be explained.

Figure 1:
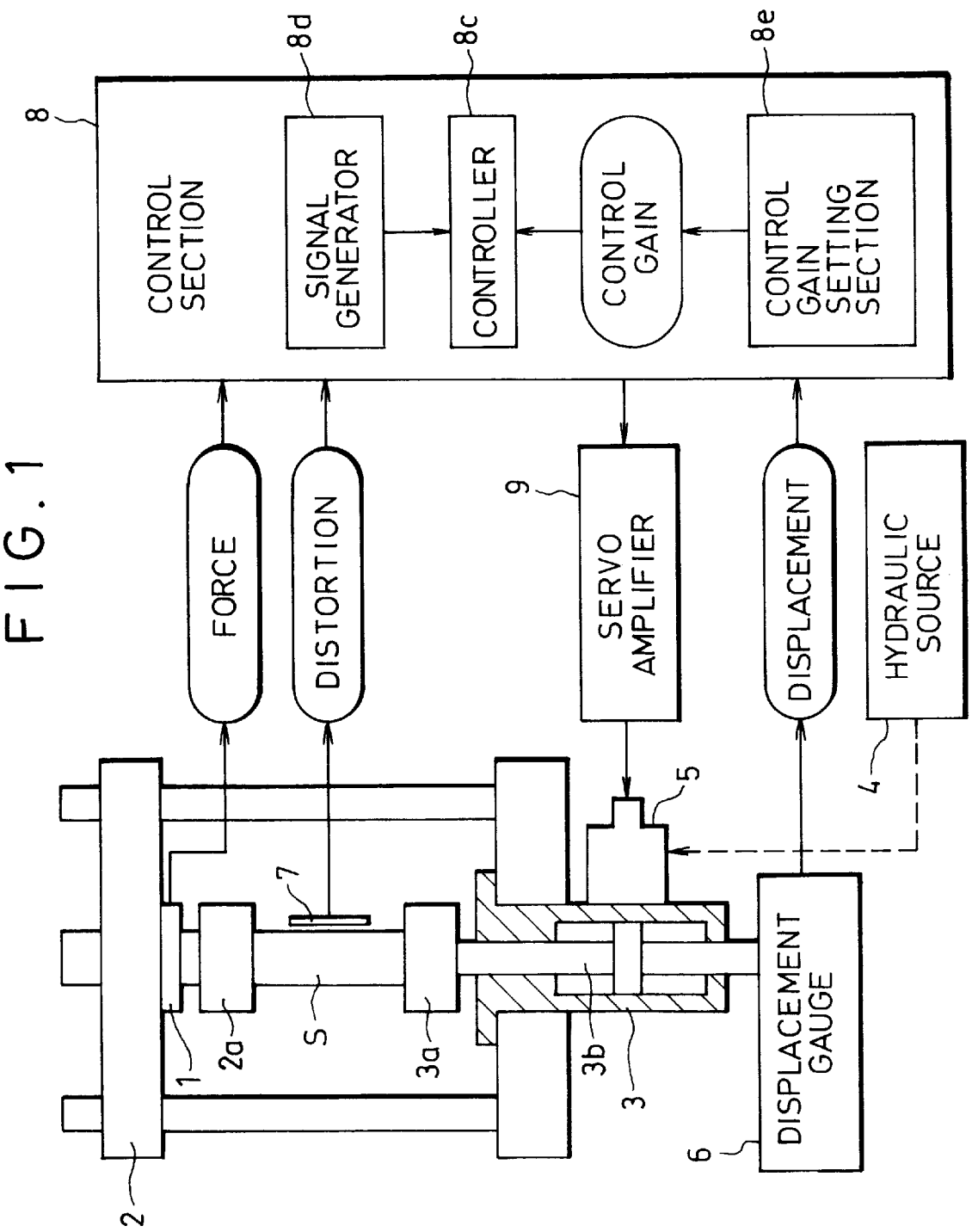
FIG. 1 is a schematic view showing the basic construction of a material testing machine according to an embodiment of the present invention.

As shown in FIG. 1, the testing machine is so configured as to supply a pressurized fluid (fluid pressure) from a hydraulic source 4 to an actuator 3, comprised of a hydraulic cylinder, through a servo valve 5 to operate a movable rod 3b of the actuator 3, thereby providing a load to a test piece S which is held between a stationary chuck 2a provided on the side of a frame of a machine body and a movable chuck 3a provided on the actuator-side. Depending on the type of material testing, the stationary chuck 2a may be removed and a die may be provided instead of the movable chuck 3a, so as to attach the test piece S between the die 3a and a load cell 1.

An actual force applied to the test piece S from the movable rod 3b is detected by the load cell 1, displacement of the test piece S is detected by a displacement gauge 6, and distortion of the test piece S is detected by a distortion gauge 7 attached to the test piece. A controller 8c of a control section 8 which is comprised of a microcomputer and the like inputs the detected force, displacement and distortion, and controls the operation of the servo valve 5 via a servo amplifier 9 in a feedback manner, with use of a control gain which is set by a control gain setting section 8e, so as to reduce an error between the force detected by the load cell 1 and a target force given from a signal generator 8d of the control section 8 to zero. The hydraulic actuator 3 is servo-controlled by the servo feedback control system to adjust a force (more generally, load) applied to the test piece S.

Figure 2:
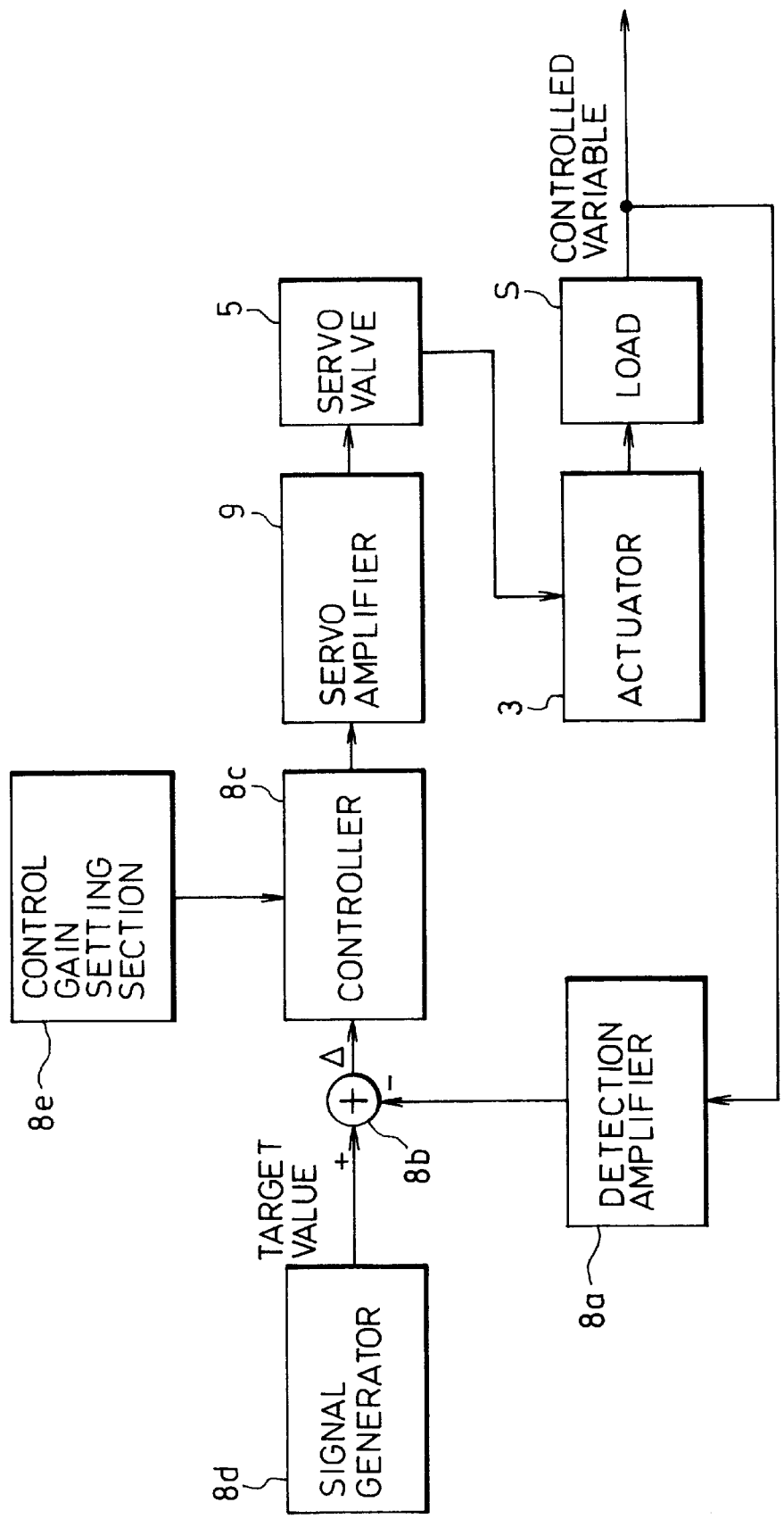
FIG. 2 is a block diagram showing a control loop in the testing machine shown in FIG. 1.

The electrohydraulic servo control system is represented by a feedback control loop, as shown in FIG. 2. More specifically, the control system comprises an error unit 8b for determining an error Δ between a control objective value (a target load or a target displacement, for example) and an output of a detection amplifier 8a which indicates a change (an actual force or an actual displacement) generated in the test piece S, and a controller 8c for controlling, via a servo amplifier 9, the operation of the servo valve 5 in accordance with the error determined by the error unit 8b. Thus, the control system controls the operation of the servo valve 5 so as to reduce the error Δ to zero, thereby hydraulically driving the actuator 3 to adjust the load applied to the test piece S.

Figure 3:
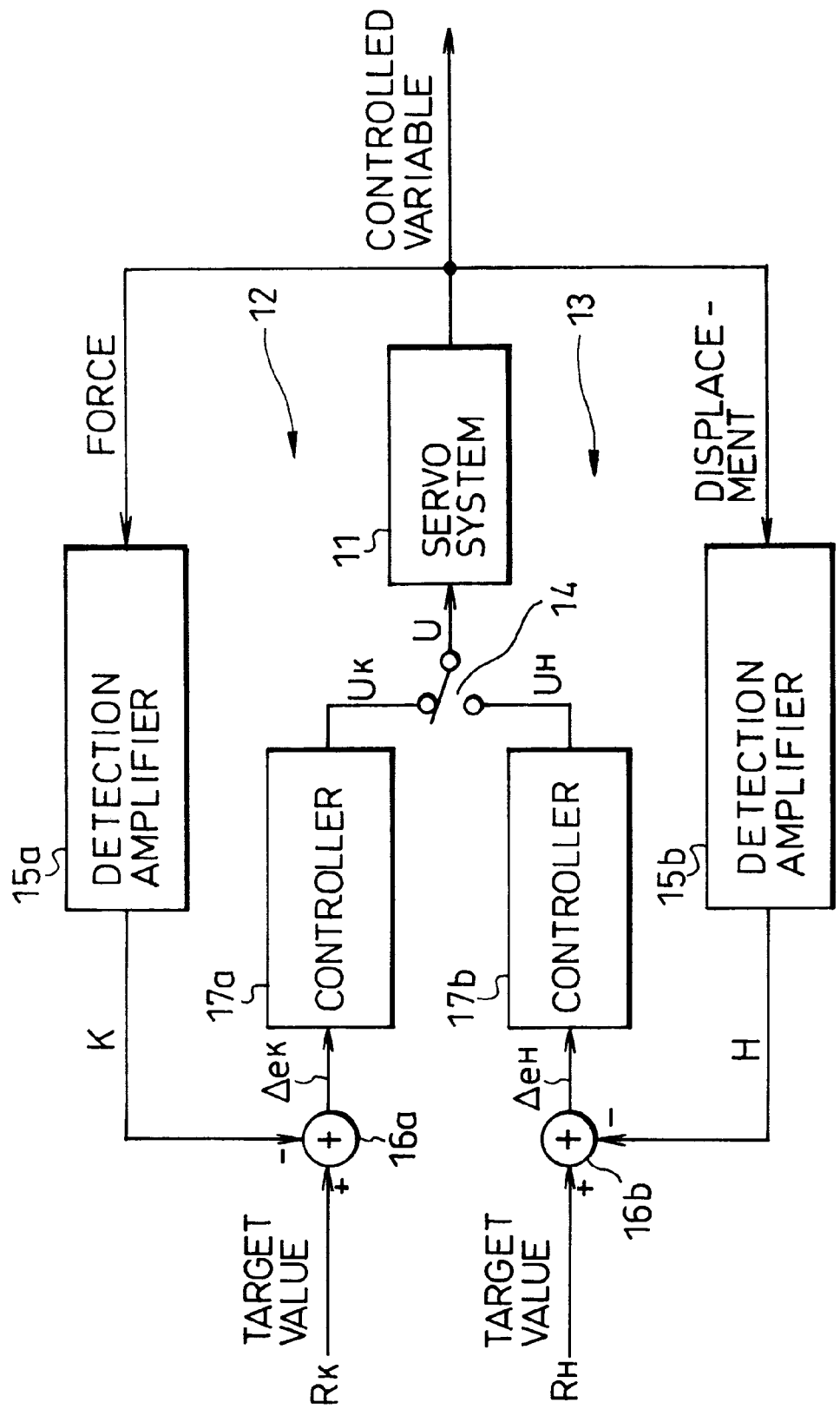
FIG. 3 is a block diagram showing the constructions of a force control system and a displacement control system of the testing machine.

As schematically shown in FIG. 3, the feedback control system of the testing machine preferably comprises a force control system 12 for feedback controlling the operation of the servo system 11, including the hydraulic actuator 3, servo valve 5 and servo amplifier 9 shown in FIG. 2, in accordance with an error ΔeK between an actual force K applied to the test piece and a target force RK; a displacement control system 13 for carrying out the feedback control in accordance with an error ΔeH between an actual displacement H of the test piece S and a target displacement RH; and a control system-changeover means (selection switch) 14 for selectively operating the force control system 12 or the displacement control system 13.

In FIG. 3, reference numeral 15a denotes a detection amplifier for detecting an actual force K from an output of the load cell 1; and 15b denotes a detection amplifier for detecting an actual displacement H from an output of the displacement gauge 6. Reference numerals 16a and 16b denote error units for determining the error ΔeK between actual force K and target force RK and the error ΔEH between actual displacement H and target displacement RH, respectively. Further, reference numerals 17a and 17b denotes controllers for generating control objective values UK and UH by multiplying the errors ΔeK and ΔeH by predetermined control gains, respectively. The controller 17a supplies the servo system 11 with the control objective value UK to carry out the feedback control in a force control mode, whereas the controller 17b supplies the servo system 11 with the control objective value UH to effect the feedback control in a displacement control mode.

The testing machine of this embodiment is featured in that the control section 8 has a function of automatically optimally setting the control gain in the feedback control loop in accordance with a mechanical property (preferably, stiffness) of the test piece S prior to the start of material testing, to thereby easily carry out material testing in respect of test pieces whose stiffness is unknown.

More specifically, in respect of the control gain automatic setting function, the testing machine has various functions which are as follows: A first function is to monitor a change in actual force applied to the test piece S or a mechanical change, i.e., a change in displacement or distortion of the test piece S. Preferably, a change in displacement is monitored. A second function is to hold a load applied to the test piece S as it is when a minute change of the test piece S, e.g., a minute displacement beyond a measurement resolution of the displacement gauge 6 is detected. A third function is to detect the actual force and the actual displacement of the test piece in a condition that the mechanical change, e.g., displacement, is stabilized. A fourth function is to estimate an elastic constant KL of the test piece S based on a relationship between the detected actual force applied to the test piece and the actual displacement of the test piece, and a fifth function is to automatically set the control gain in the feedback control loop in accordance with the estimated elastic constant KL.

Figure 4:
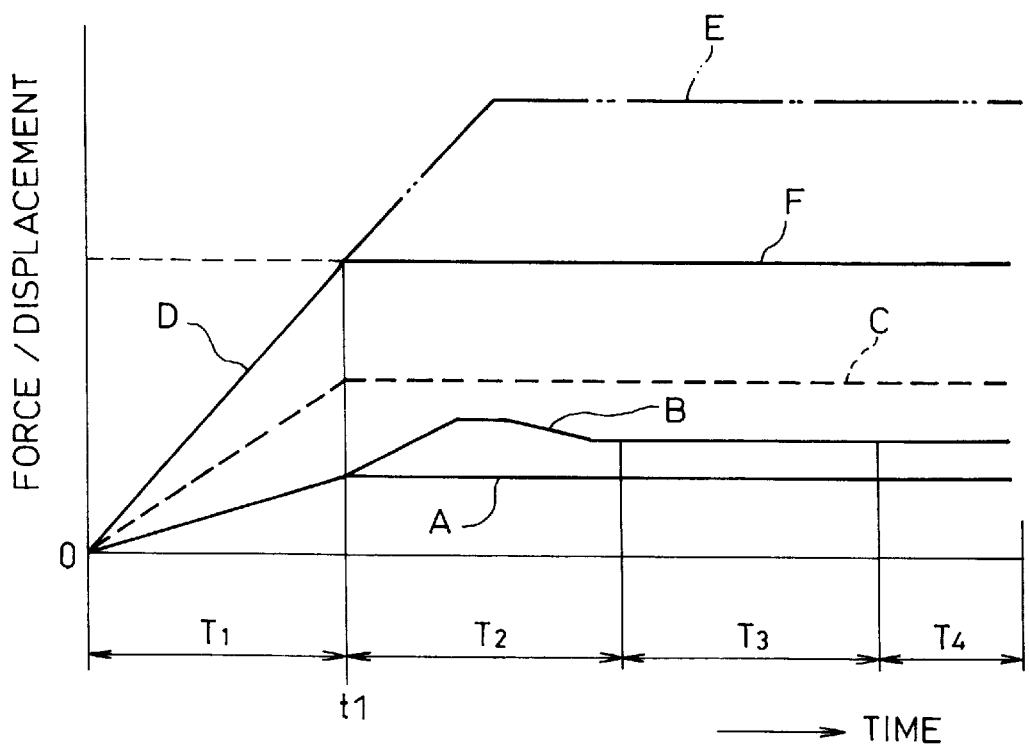
FIG. 4 is a graph showing changes in the force applied to a test piece, the control gain, and the displacement of the test piece with elapse of time during automatic control gain setting processing in the testing machine shown in FIG. 1.

In an automatic control gain setting processing performed by the testing machine, the operation of the actuator 3 is controlled while gradually increasing the control gain in the feedback control loop from its minimum value, as shown by the dotted line C in FIG. 4, to thereby gradually increase the load, e.g., force, applied to the test piece S, as shown by the solid line D in FIG. 4. The application of force is continued until a minor displacement slightly beyond the measurement resolution of the displacement gauge 6 is detected (processing time period T1). A maximum force applicable to the test piece S in the automatic control gain setting processing is preferably restricted up to a value which is 30 to 50% of a maximum target force (shown by the horizontal line portion of the two-dotted-chain line in FIG. 4) for material testing effected after the automatic control gain setting processing, so as to prevent the test piece S from being applied with a large force during the control gain setting. The maximum force permitted in the control gain setting may be determined by an estimated mechanical property of the test piece S.

If a minute displacement of the test piece S is detected while the force is applied thereto, the operational state of the actuator 3 is held for a predetermined period of time (processing time period T2), thereby holding the force applied to the test piece S at that time, until the displacement of the test piece S is stabilized, as shown by the solid line F in FIG. 4. For the test piece S which is large in stiffness or elastic constant KL, the displacement of the test piece is stabilized within a relatively short period of time, as shown by the time-dependent displacement characteristic line A in FIG. 4. For the test piece S which is small in stiffness or elastic constant KL, the test piece displacement is stabilized after it changes to a certain extent, as shown by the characteristic line B in FIG. 4. The time period T2 during which the force is kept unchanged is determined to have a sufficient time length by taking account of the fact that the time period required for the test piece to be stabilized varies depending on the elastic constant of the test piece.

Subsequently, the actual force and the actual displacement of the test piece are detected a multiple number of times (processing time period T3) each. The force/displacement detection is repeatedly carried out 100 to 200 times, for instance, to cancel out detection errors. Then, an average of detected forces and an average of detected displacements are determined, and the elastic constant KL of the test piece S is estimated by dividing the average force by the average displacement (processing time period T4). By looking up a table which is prepared beforehand and which indicates the relationship between elastic constants and optimum control gains, an optimum control gain to be set in the feedback control loop is determined based on the estimated elastic constant KL, and the determined optimum control gain is initially set.

To determine the relationship between elastic constants and optimum control gains, optimum control gains in respect of various test pieces S whose elastic constants are known are determined in advance, while optimally operating the testing machine under the control of the servo control system of the machine. Then, by arranging these pieces of data, tabulated data indicating the relationship which is proper to the servo control system is obtained. Furthermore, if a new relationship between the elastic constant KL and the optimum control gain is attained during the material testing, the testing machine learns such actual data and renews the table data.

In the following, the relationship between the elastic constant KL indicative of the stiffness of the test piece and the optimum control gain in the servo control system will be explained.

The optimum control gain for the control loop to stably operate the servo system, which in turn operates the hydraulic actuator 3, varies depending on the stiffness (elastic constant) of the test piece S and is proper to the control loop. The control loop of the testing machine is configured as a closed-loop transfer system which includes, as shown in FIG. 2, the servo amplifier 9, servo valve 5, actuator 3 and test piece S (load).

Thus, to realize a stabilized operation of the servo system, the optimum control gain should be set, e.g., in the controller 8c, by taking the transfer system (transfer function) proper to the testing machine and the load transfer system (transfer function) which depends on mechanical properties of the test piece S.

Figure 5:
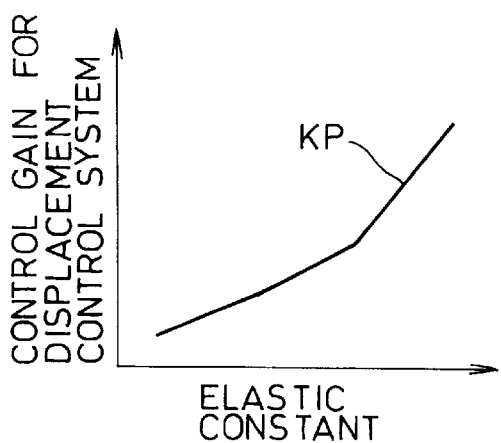
FIG. 5 is a graph showing a relationship between optimum control gain and elastic constant of the test piece for the displacement control system shown in FIG. 3.
Figure 6:
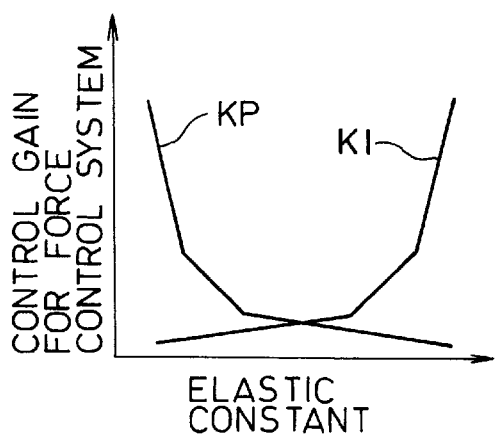
FIG. 6 is a graph showing a relationship between optimum control gain and elastic constant of the test piece for the force control system shown in FIG. 3.

FIG. 5 exemplarily shows the optimum control gain, corresponding to the elastic constant KL of the test piece S, in the displacement control system in which the operation of the actuator 3 is servo-controlled based on the displacement of the test piece S. In FIG. 5, the optimum proportional gain KP for the displacement control system is shown as a function of elastic constant KL. An optimum elastic constant KL vs. integral gain KI characteristic line is similar to that shown in FIG. 5 for the proportional gain KP. FIG. 6 shows, by way of example, the optimum proportional gain KP and the optimum integral gain KI, corresponding to the elastic constant KL of the test piece S, for the force control system in which the operation of the actuator 3 is servo-controlled based on the force applied to the test piece S.

Prior to the automatic control gain setting processing, the testing machine is operated with use of a large number of test pieces S whose elastic constants KL, as a whole, vary to cover the entire elastic constant region in which elastic constants of various test pieces to be subject to material testing vary. During the operation of the testing machine, the proportional gains KP and integral gains KI for the displacement control system and the force control system are so tuned as to make it possible for the control system of the machine to operate in an optimum manner, whereby optimum control gains KPi and KIi for various elastic constants KLi (i=1, 2, - - - , N) are attained, and pieces of data which indicate the relationship between these elastic constants KLi and the optimum control gains KPi, KIi are tabulated as shown, by way of example, in FIG. 7. The optimum control gains KP and KI, proper to the testing machine, shown in FIGS. 5 and 6 and corresponding to the elastic constant KL of the test piece S concerned, are determinable based on the tabulated data, as will be explained hereinbelow.

In the automatic control gain setting processing effected prior to the start of material testing, a force applied to the test piece S is caused to gradually increase until a minute displacement of the test piece S is detected, as mentioned before, in order to estimate the elastic constant K of the test piece S. In light of the relationship between the elastic constant KL and the proportional gain KP found at the time of step response of the force control system and shown by way of example in FIG. 8, it is understood that a proper control of force applied to the test piece S, especially, in the case of the test piece whose elastic constant is unknown, can be made by gradually increasing the proportional gain KP with elapse of time, as shown by way of example in FIG. 9. More specifically, as shown in FIG. 4, for instance, to variably control the force applied to the test piece in accordance with a target force changing pattern which is represented by a ramp hold wave form where a maximum force is restricted, the initial value of the proportional gain KP is set to a minimum value, suitable for a test piece having a largest stiffness, of the proportional gain KP, and then the proportional gain KP is gradually increased with elapse of time. During the force control, the integral gain KI is set to zero, for instance.

FIG. 10 shows the relationship between the elastic constant KL and the proportional gain KP observed at the time of step response of the displacement control system. With use of this relationship, a displacement control may be made instead of the force control in the automatic control gain setting. In this case, a displacement is given to the test piece S under the displacement control, while gradually increasing the proportional gain KP with elapse of time. As in the automatic control gain setting under the force control, a load state is temporally held unchanged when a minute displacement of the test piece S is detected.

A further explanation as for the automatic control gain setting under the force control mode will be given.

When a minute displacement of the test piece S beyond the measurement resolution of the displacement gauge 6 is detected while applying the load (force) to the test piece S as mentioned above, the proportional gain and the control objective value, for instance, observed when the minute displacement is detected are kept unchanged. As a result, the load (force) applied to the test piece S is kept unchanged, thereby preventing the test piece from being applied with an undesired force. Under the condition where the load is maintained unchanged, the testing machine waits until the test piece displacement is stabilized. As seen from FIG. 12 showing the time period required for the displacement to become stabilized at the time of step response, the required time period therefor varies depending on the elastic constant KL of the test piece S. In this connection, the force holding time period T2 is set based on the time period required for the stabilization of displacement of the test piece having smallest elastic constant KL among those test pieces to be subject to material testing.

After waiting the stabilization of test piece displacement, the displacement of the test piece and the force applied thereto are each periodically detected a multiple number of times, and an average test piece displacement and an average force are determined. By determining the average of these measurement values, a variation in the measured values, resulting from external disturbance or the like, is reduced. Subsequently, the elastic constant of the test piece S is estimated by dividing the average force by the average test piece displacement. In the present embodiment, an estimation is made as for the elastic constant KL of the test piece S based on the relationship between the force and displacement which are observed when a minute test piece displacement is caused to be generated as a result of applying a slight load (force) to the test piece S.

After estimating the elastic constant KL, a control gain corresponding to the estimated elastic constant KL is determined from the aforementioned table in a manner of inverse operation, whereby optimum control gains KP and KI to be set in the control system can be determined. In other words, the automatic setting can be achieved to determine the optimum control gain for material testing even in respect of the test piece whose elastic constant KL is unknown.

Figure 13:
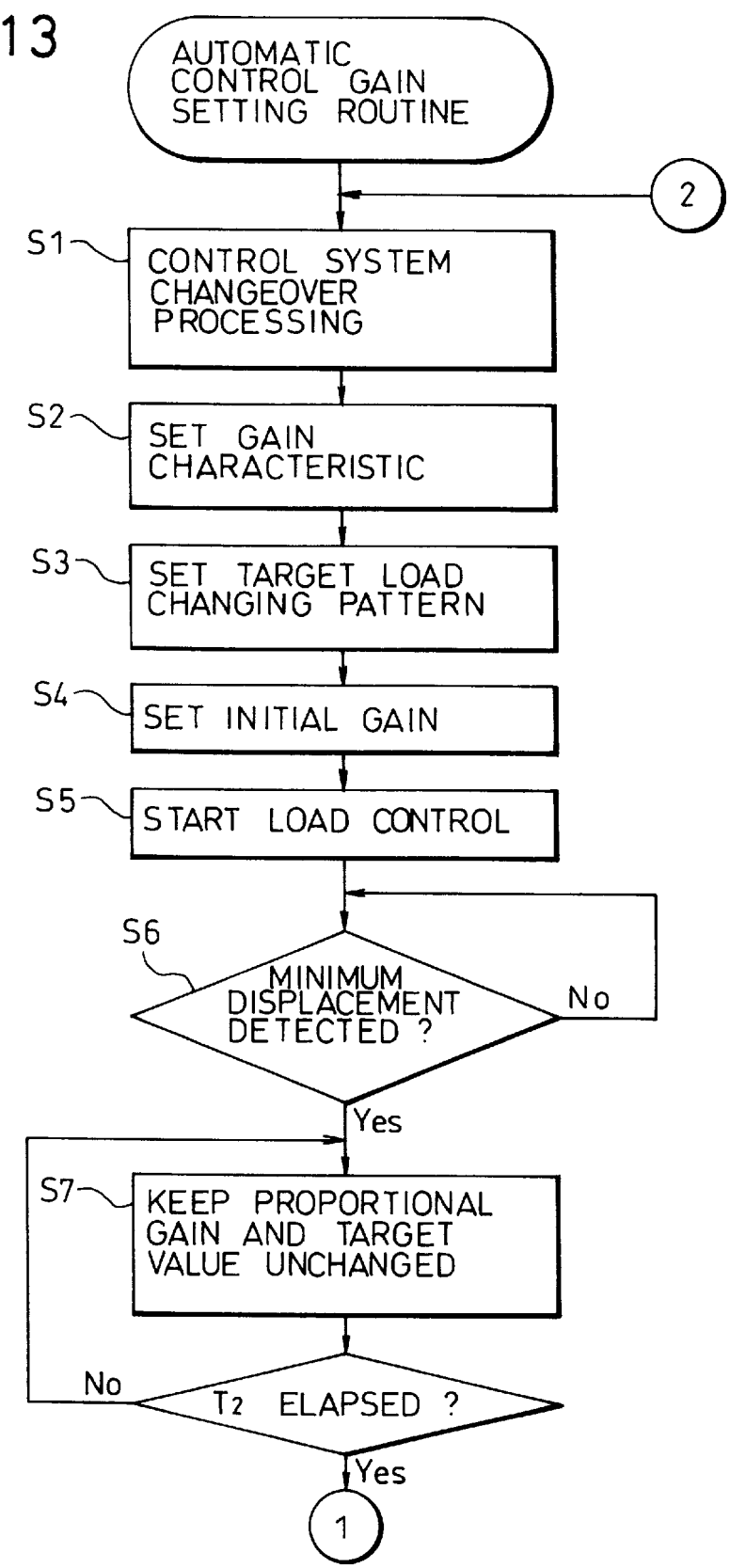
FIG. 13 is a flowchart showing part of an automatic control gain setting routine executed by a control section of the testing machine shown in FIG. 1.
Figure 14:
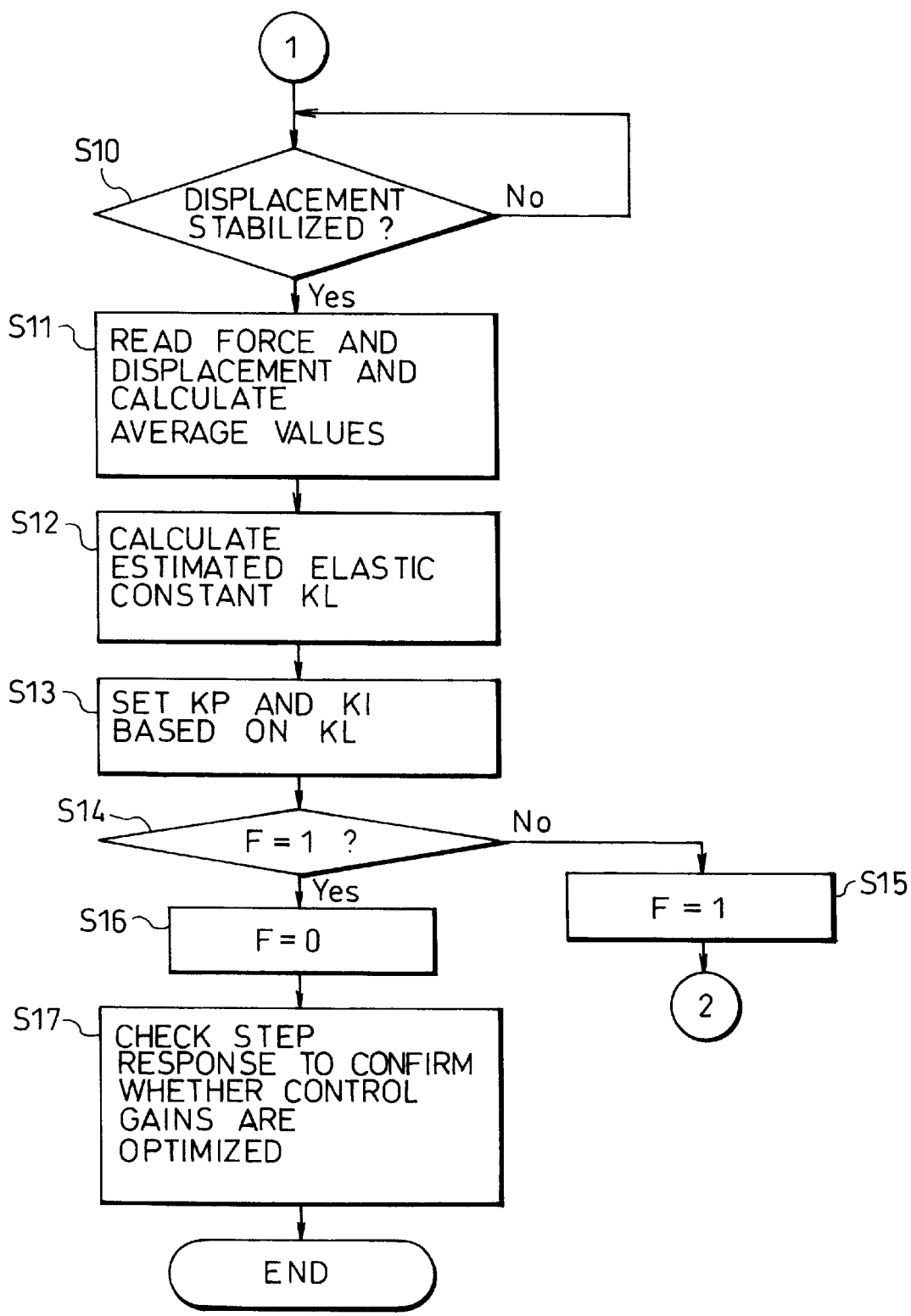
FIG. 14 is a flowchart showing the remaining part of the automatic control gain setting routine.
Figure 15:
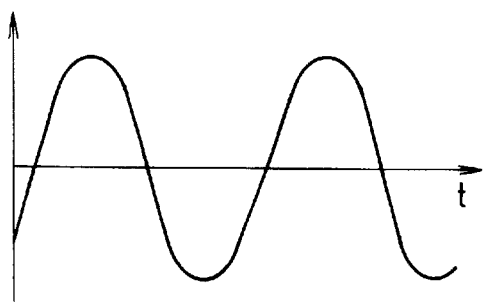
FIG. 15 is a graph showing a sinusoidal wave signal which is given as a target load in a fatigue test.

With reference to FIGS. 13 and 14, an example of processing procedure performed by the control section 8 in the automatic control gain setting will be explained.

The control section 8 carries out the processing for control system changeover (step S1). In the control system changeover processing, the control system changeover means 14 shown in FIG. 3 is caused to perform a changeover action, thereby selecting one of the controllers 17a and 17b, e.g., the controller 17a of the force control system.

If the force control system is selected at step S1, a time elapse vs. gain characteristic for gain adjustment (corresponding to the slanted portion of the dotted line C in FIG. 4) is set as shown in FIG. 9 (step S2), and a target force changing pattern for gain adjustment is set to be equal to a ramp hold waveform which is shown in FIG. 4 by a combination of the solid line D and the two-dotted chain line E (step S3). Next, after setting an initial gain (minimum value) for the force control system (step S4), a force control is started which is carried out in accordance with the time elapse vs. gain characteristic and the target force changing pattern (step S5).

Based on the actual displacement of the test piece S detected by the displacement gauge 6, a determination is made as to whether or not a minimum displacement which is measurable by the displacement gauge 6 is detected (step S6). If the minimum test piece displacement is detected (the time point of t1 shown in FIG. 4), the proportional gain and the target force at the time point of t1 are kept unchanged, as shown by the dotted line C and the solid line F in FIG. 4 (step S7). As a result, the actual force applied to the test piece S1 at the time point of t1 is kept substantially unchanged. Next, a determination is made as to whether or not the predetermined time period of T2 for stabilizing the test piece displacement has elapsed from the time point of t1(step S8). If the time period of T2 has not elapsed, the control flow returns to step S7 where the proportional gain and the target force are maintained, and the actual displacement of the test piece S detected by the displacement gauge 6 is read by the controller 17a.

If it is determined at step S8 that the time period of T2 has elapsed from the time point of t1 at which the minimum displacement was detected, a determination is made based on the tendency of a change in the actual test piece displacement as to whether or not the actual displacement of the test piece S is stabilized (step S10 in FIG. 14). Ordinarily, the actual test piece displacement is stabilized when the time period of T2 has elapsed. However, if it is determined at step S10 that the actual test piece displacement has not been stabilized as yet, the controller waits for the test piece displacement being stabilized.

If it is determined at step S10 that the actual displacement of the test piece S has been stabilized, the output of the load cell 1 indicative of the actual force applied to the test piece S is periodically read a multi-number of times, e.g., 200 times, and the output of the displacement gauge 6 indicative of the actual displacement of the test piece is periodically read a multi-number of times, e.g., 200 times. Then, an average value of the detected actual forces and an average of the detected actual displacements are calculated (step S11). Next, an estimated elastic constant KL of the test piece S is calculated based on the average actual force and the average actual displacement (step S12), and the optimum proportional gain KP and optimum integral gain KI for the force control mode, suited to the elastic constant, are determined based on the estimated elastic constant KL and set in the controller 17a of the force control system (step S13).

Next, a determination is made as to whether or not a flag F has a value of 1 which indicates that a shift is made from the setting of the control gain for one of the force and displacement control systems to the control gain setting in respect of the other control system (step S14). If the flag value is not at 1, the flag F is set to a value of 1 (step S15). The control flow returns to step S1 of FIG. 13 to carry out the control system changeover processing. In this illustrative example where the control gain setting for the force control system is finished, a shift is made to the control gain setting processing for the displacement control system.

The control gain setting processing for the displacement control system is carried out as in the case of the force control system. More specifically, at step S2, the time elapse vs. gain characteristic shown in FIG. 10 is set, and, at step S3, a target displacement changing pattern (not shown) similar to the target force changing pattern of FIG. 4 is set. Here, the target displacement has its initial value set to be equal to the sum of the actual test piece displacement observed at the completion of the control gain setting for the force control system and an initial value of the target displacement determined by the target displacement changing pattern.

Next, at step S4, the initial control gain for the displacement control system is set, and at step S5, the displacement control is started. If it is determined at step S6 that a minimum displacement of the test piece S (here, a displacement equal to the sum of the actual test piece displacement observed at the completion of the control gain setting for the force control system and the minimum displacement) is detected, both the control gain and the target displacement observed when the minimum displacement is detected are kept unchanged for a predetermined time period, at steps S7 and S8. After elapse of the predetermined time period, it is determined at step S10 that the actual test piece displacement is stabilized, the average values of both the actual force applied to and the actual displacement of the test piece S are calculated at step S11, and the elastic constant of the test piece is estimated based on the average actual force and the average actual displacement at step S12. Then, at step S13, the proportional gain KP and the integral gain KI, suited to the estimated elastic constant, for the displacement control mode are set in the controller 17b of the displacement control system.

Since the result of determination at step S14 becomes affirmative, the flag F is reset to a value of 0 at step S16, and the step response or the like is determined to confirm whether or not the control gains are optimized at step S17, whereupon the control gain setting processing is completed. More specifically, at step S17, the step response in the force control system and the step response in the displacement control system are checked, while setting the step input of target force and the step input of target displacement so as not to apply an excessive load to the test piece S and carrying out the control system changeover processing where required.

Subsequently, with use of the control gain automatically set, a desired one or more of fatigue test, creep test, relaxation test, tensile test and compression test are carried out.

With the testing machine of this embodiment, an optimum control gain suited to mechanical properties of the test piece S can be easily set within a short period of time, as explained above, even if mechanical properties of the test piece such as stiffness (elastic constant) are unknown. In addition, the elastic constant KL can be determined without applying an excessive load to the test piece S, so that an optimum control gain setting may be achieved under a simplified control algorithm. Particularly, since the elastic constant KL is estimated based on sampled data in respect of the force and displacement of the test piece, obtained by sampling them a multi-number of times after the displacement of the test piece applied with a slight load is stabilized, the estimation can be made with a sufficiently high accuracy. Further, since the control gain best suited to the control system is determined by inverse operation based on the estimated elastic constant and is set therein, the automatic control gain setting can be made efficiently.

The automatic control gain setting processing of the present embodiment can be modified variously.

For instance, in view of the fact that the force to be applied to and the displacement to be generated in the test piece, may vary depending on the type of material testing, the time elapse vs. gain characteristic or the target load changing pattern, especially, a maximum applied force in this pattern, may be set by taking account of the type of material testing.

Figure 16:
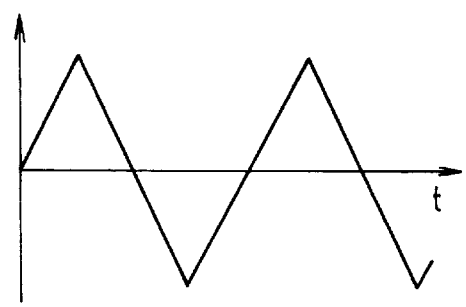
FIG. 16 is a graph showing a triangular wave signal indicative of a target load in a fatigue test.
Figure 17:
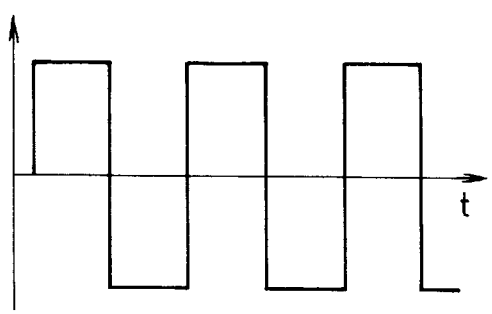
FIG. 17 is a view showing a rectangular wave signal indicating a target load in a fatigue test.
Figure 18:
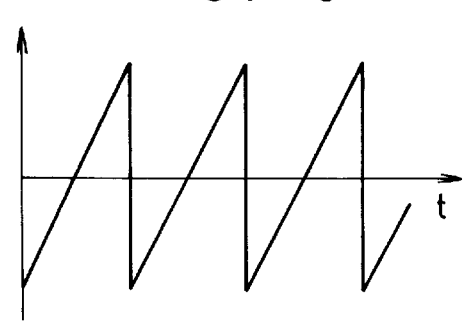
FIG. 18 is a graph showing a ramp wave signal which indicates a target load in a fatigue test.
Figure 19:
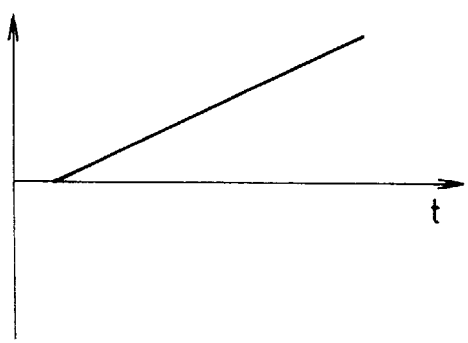
FIG. 19 is a graph showing a ramp wave signal which indicates a target load in a tensile test.
Figure 20:
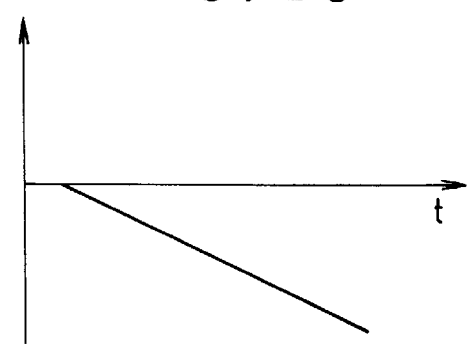
FIG. 20 is a graph showing a ramp wave signal indicative of a target load in a compression test.
Figure 21:
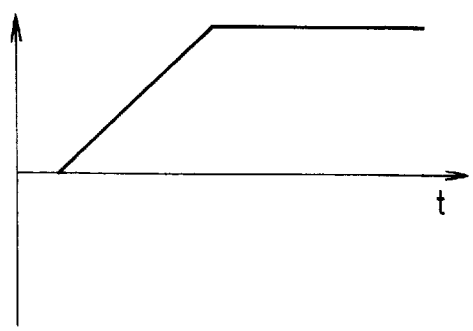
FIG. 21 is a graph showing a ramp-hold wave signal indicative of a target load in a creep-relaxation compression test.

More specifically, in the case of fatigue test, the force applied to the test piece S is caused to vary in the form of triangular wave as shown in FIG. 16, and in the case of creep-relaxation test, the force is caused to increase in the form of ramp wave and is then caused to be kept unchanged, as shown in FIG. 21. Further, in the case of tensile or compression test, the force or displacement is caused to increase at a fixed slope, as shown in FIG. 19 or 20. By taking account of the above differences among the types of material testing, the elastic constant may be estimated based on the relationship between the displacement and force detected after the test piece displacement is stabilized in a condition that the test piece is applied with the force which corresponds to 30 to 50% of the maximum value of the target force to be applied to the test piece S in material testing.

Further, in the testing machine configured to periodically measure the test piece displacement for the estimation of elastic constant while keeping the target force unchanged after a minute test piece displacement slightly beyond the measurement resolution of the displacement gauge 6 is detected, the detected displacement can be greatly affected by noise. To reduce the noise affection, the periodically detected displacements may be subject to filtering based on moving average method, and it may be determined that a significant displacement is generated in the test piece attributable to the application of load (force), if a predetermined displacement is successively detected a multi-number of times.

In the case of determining the control gain by searching the table in which only a small quantity of data showing the relationship between elastic constants and control gains is stored, an approximate optimum control gain may be determined in accordance with an approximation formula determined by the small quantity of data, on the basis of an estimated elastic constant determined by an average force and an average displacement.

Moreover, the control gain for a distortion control system can be automatically determined, while carrying out a distortion control with use of distortion generated in the test piece S as a controlled variable.

A further feature of the material testing machine according to the present embodiment will be explained.

In addition to the function of effecting the automatic control gain setting prior to material testing, the testing machine has a function of correcting a predetermined control gain for the feedback control effected during the material testing, in accordance with a mechanical change (stiffness change) generated in the test piece S, to thereby optimize the feedback control gain during the material testing.

The correcting function is achieved by measurement means for periodically measuring the actual force applied to and the actual displacement generated in the test piece S, estimation means for estimating the elastic constant of the test piece on the basis of the relationship between the measured force and the measured displacement, and correction means for correcting and optimizing the control gain having been set in accordance with the estimated elastic constant.

After optimally initializing the control gain for the control section 8 (more generally, for the feedback control loop) by means of the aforementioned automatic control gain setting, material testing in respect of the test piece S is started with use of the optimally initialized control gain. More specifically, fatigue test, creep test, relaxation test, tensile test or compression test in respect of the test piece S is selectively carried out by variably controlling the target load for the control system with use of a signal generator (shown by reference numeral 8*d* in FIG. 1).

Figure 22:
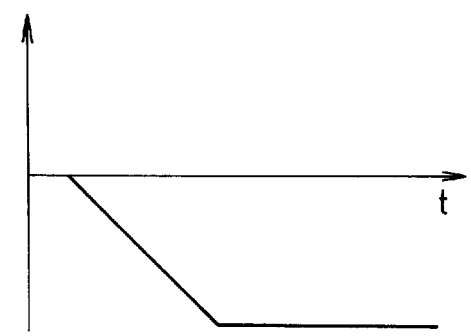
FIG. 22 is a graph showing a ramp-hold wave signal indicating a target load in a creep-relaxation tensile test.

In the case of fatigue test, a testing waveform which periodically changes in a specific pattern, such as sinusoidal wave, triangular wave, rectangular wave or ramp wave shown in FIGS. 15 to 18, is generated by the signal generator 8*d* and is supplied, as the control objective value, to the controller 8*c* of the control section 8. As a result, the target value of the load to be applied to the test piece S periodically changes, so that the fatigue test is carried out. For tensile test or compression test, a ramp wave shown in FIG. 19 or 20 is given as the target value. A ramp-hold wave shown in FIG. 21 or 22 is given as the target value for creep-relaxation compression/tensile test.

During the material testing, especially, fatigue test (dynamic test) using a testing waveform which periodically changes in a specific pattern, the control gain set for the control section 8 (more generally, for the servo control system) sometimes deviates from it optimum value if mechanical properties (stiffness) of the test piece S change as the material testing proceeds. The deviation of the control gain from the optimum value causes the load actually applied to the test piece to change, thereby lowering the testing accuracy.

More specifically, as the load (force) periodically changes in its amplitude (width) during the material testing, the changing width of the actual load (actual force) applied to the test piece and the level of the actual load (actual average force) sometimes vary, thereby causing the test condition to vary. This naturally causes an error in the material testing and hence lowers the accuracy and reliability of the material testing.

In the testing machine of the present embodiment, a change in the elastic constant KL of the test piece S is monitored during the course of fatigue test carried out with use of a predetermined control gain which was set in the servo control system, by measuring, at intervals of a predetermined cycle, the load applied to and the displacement generated in the test piece S and by periodically estimating the elastic constant KL based on the relationship between the detected force and displacement. If a change in the elastic constant KL of the test piece S is detected, an optimum control gain suited to a new elastic constant KL of the test piece is determined by searching the aforementioned table, for instance, and the control gain previously set in the servo control system is corrected so as to be optimized.

Figure 23:
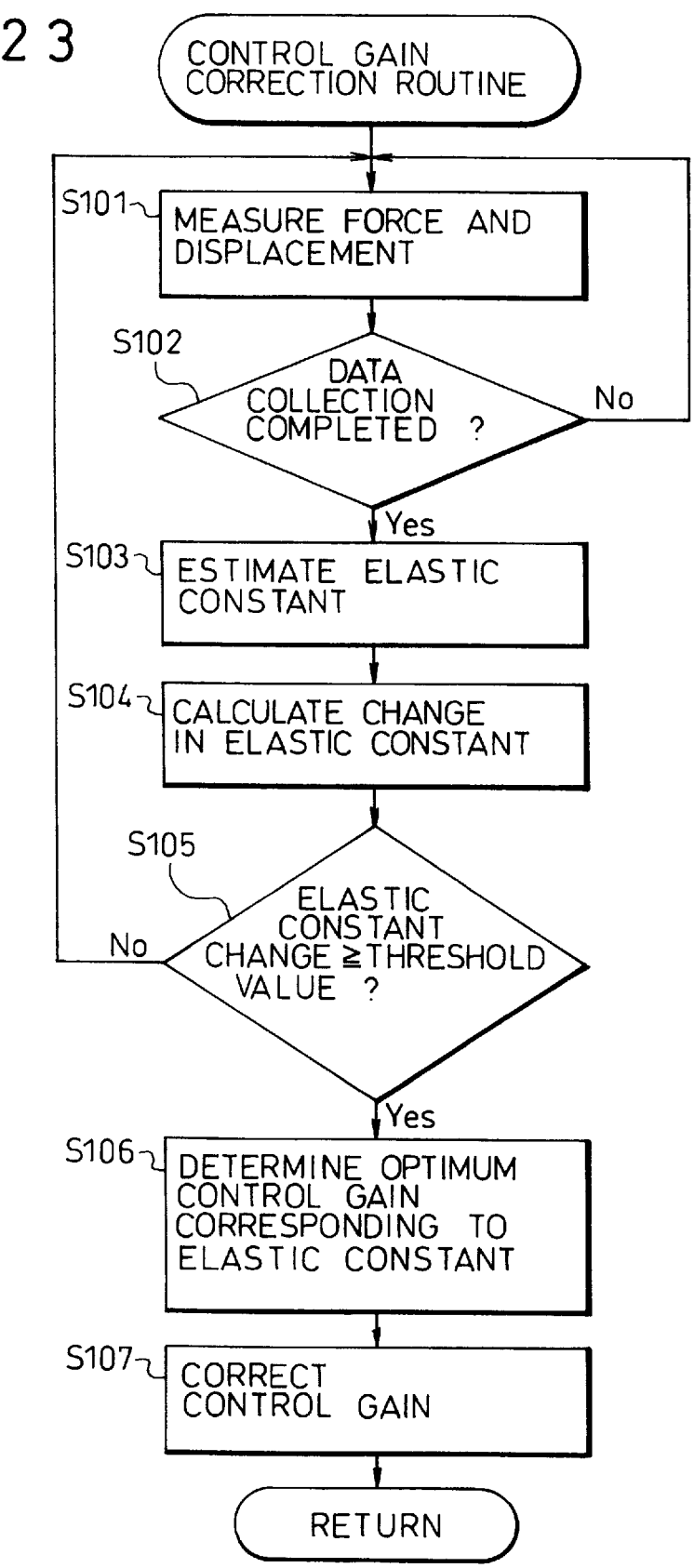
FIG. 23 is a flowchart showing a control gain correction routine executed by the controller of the testing machine shown in FIG. 1.

More specifically, a control gain correction routine shown in FIG. 23 is executed by the control section 8 during the material testing.

In this control gain correction routine, the force applied to the test piece S and the displacement generated by the applied force in the test piece S are measured at intervals of a cycle which is sufficiently shorter than the cycle at intervals of which the force applied to the test piece S periodically varies, e.g., measured at intervals of a cycle (100 μsec, for instance) at which the control section 8 carries out its operation (step S101). Then, a determination is made as to whether or not a predetermined number of data samples in respect of each of the force and the displacement is attained (step S102). If it is determined that a sufficient number of data samples is attained, an average force and an average displacement are determined, and the elastic constant KL of the test piece S is estimated based on these average values (step S103).

Subsequently, the difference ΔKL between the estimated elastic constant KL and an elastic constant corresponding to the control gain currently set in the servo control system, i.e., a change in elastic constant caused by a change in the load state of the test piece S is determined (step S104). Next, a determination is made as to whether or not the elastic constant change ΔKL exceeds a predetermined threshold value (step S105). The threshold value serves to prevent an excessively frequent correction of control gain which would be otherwise corrected even if the elastic constant slightly changes. If the elastic constant change ΔKL exceeds the threshold value, an occurrence of a significant change in the elastic constant is determined, and an optimum control gain corresponding to the newly estimated elastic constant KL is determined by searching the table in which the relationship between elastic constants and optimum control gains is stored (step S106).

After determining the optimum control gain corresponding to the new elastic constant of the test piece S, the thus determined optimum control gain is set in the servo control system, to thereby correct the control gain previously set therein (step S107). The control gain correction is carried out at timing which is synchronized with the cycle at which the target force for the servo control system periodically varies.

As explained in the above, if the elastic constant KL of the test piece S changes during the material testing, the optimum control gain suited to the changed elastic constant is determined and is set in the servo control system, whereby the control gain set therein is optimally corrected.

With the testing machine having the function of optimally setting the control gain for the servo control system, the control gain is optimally corrected in accordance with the elastic constant of the test piece S estimated during the course of the material testing, if the control gain deviates from its optimum value as the mechanical properties (elastic constant KL) of the test piece S change while the material testing proceeds after the start of the testing which was started in a condition that an optimum control gain was set by means of the aforementioned automatic control gain setting.

In the case of a material testing machine which lacks the function of automatically setting the control gain prior to material testing, by providing such a machine with the control gain correction function of this embodiment, the control gain can be optimized in accordance with the elastic constant of the test piece S estimated during the course of the testing even if an error between the optimum control gain and the control gain initially set in a trial and error manner is considerably large.

With the control gain optimizing function, the control gain for the servo control system is always optimized, so that the material testing can be carried out with the operation of the control system stabilized, thereby highly improving the testing accuracy. Furthermore, the control gain is optimally corrected only if the elastic constant KL of the test piece S changes beyond the threshold value, i.e., only if a significant error is found in the control gain setting. Thus, the control gain correction is made without being extremely sensitive to a slight change in the elastic constant of the test piece S. This makes it possible to optimize the control gain to thereby keep the control system stabilized, whereby the material testing can be made highly accurately.

The control gain correction of the present embodiment can be modified in various manners.

For instance, in the embodiment, optimum control gains corresponding to elastic constants KL of various test pieces are stored in advance in the table and the optimum control gain suited to the estimated elastic constant is determined by searching the table. Instead, the optimum control gain suited to the elastic constant KL may be derived by means of approximate calculation with use of an arbitrary-degree polynomial approximate equation given in advance and showing the optimum control gain as a function of elastic constant.

It is not inevitably necessary to carry out the automatic control gain setting processing in the initial setting of the control gain for the servo control system. Instead, the initial value of the control gain may be set by changing, in a trial and error manner, the control gain once set by taking account of an experientially estimated elastic constant. Alternatively, the initial control gain may be set based on the already-known data in respect of the test piece S, such as elastic constant data. Moreover, in the case of a material testing machine configured to generate a testing waveform indicative of target force, the level or amplitude of the testing waveform may be corrected in the control gain correction.

In the following, a further feature of the material testing machine of the present embodiment will be explained.

The testing machine of this embodiment is designed to select either the force control system 12 or the displacement control system 13 by means of the control system changeover means 14, as shown in FIG. 3, to thereby feedback-control the servo system 11 in either force control mode or displacement control mode.

In order to feedback-control a load which is applied from the hydraulic servo system (process) 11 to a test piece S, the force control system 12 generates a control output value Uk for the servo system 11 in accordance with the error $\Delta e_K$ between the force applied to the test piece S and a target force value Rk. More specifically, the controller 17a of the force control system 12 determines the control output value Uk in accordance with formula (1) given by:

$$U_K = P_K \cdot \Delta e_K + I_K \cdot \Sigma K \quad (1)$$

where Pk and Ik indicate a proportional control gain and an integral control gain which are set in advance, and $\Sigma K$ indicates the integral of the error $\Delta e_K$.

The displacement control system 13 generates a control output value UH for the servo system 11 in accordance with the error $\Delta eH$ between the actual displacement of the test piece S and the target displacement value RH. More specifically, the controller 17b of the displacement control system 13 determines the output control value UH in accordance with formula (2) given by:

$$U_H = P_H \cdot \Delta e_H + I_H \cdot \Sigma H \quad (2)$$

where PH and IH are a proportional control gain and an integral control gain which are set beforehand, and $\Sigma H$ indicates the integral of the error $\Delta e_H$.

As shown in formulas (1) and (2), the feedback control for the servo system 11 is carried out in the form of PI control where the differential term in PID control is set to zero. Alternatively, the differential control gain may be set to carry out PID control.

Figure 24:
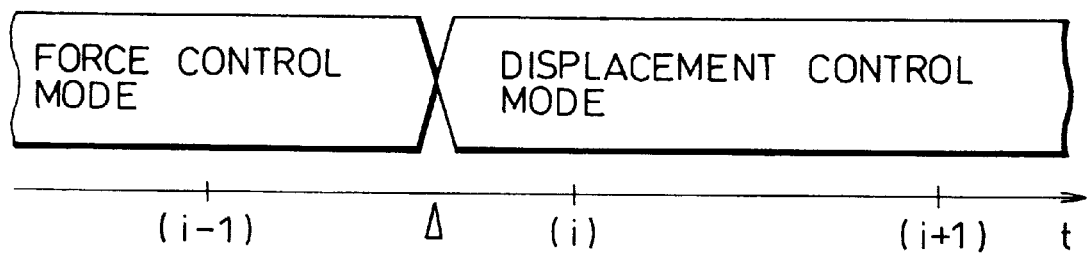
FIG. 24 is a conceptual view showing a changeover from a force control mode to a displacement control mode in the material testing machine.

In the testing machine of this embodiment having dual control system comprised of the force control system 12 and the displacement control system 13 and adapted to selectively operate either one of these control systems to control the operation of the servo system 11, the changeover of control system is performed when instructions are give by an operator in the course of material testing in respect of the test piece S. For instance, a shift is made from the force control mode where the actual force applied to the test piece is controlled to the target force to the displacement control mode where the actual displacement of the test piece S is controlled to the target displacement, as shown in FIG. 24. Conversely, a shift is made from the displacement control mode to the force control mode, as shown in FIG. 25.

On the occasion that the control mode is changed over, the control output value U with which the operation of the servo system 11 is controlled greatly varies at the time of mode changeover due to the difference of control gain between the force control system 12 and the displacement control system 13. As a result, the load applied to the test piece S abruptly changes, so that an undesired shock may be applied to the test piece. To obviate this, heretofore, the load applied to the test piece is released once, e.g., by resetting the load to zero. On the contrary, the material testing machine of this embodiment achieves the control mode changeover in a way mentioned below, without causing a shock to the test piece.

Figure 25:
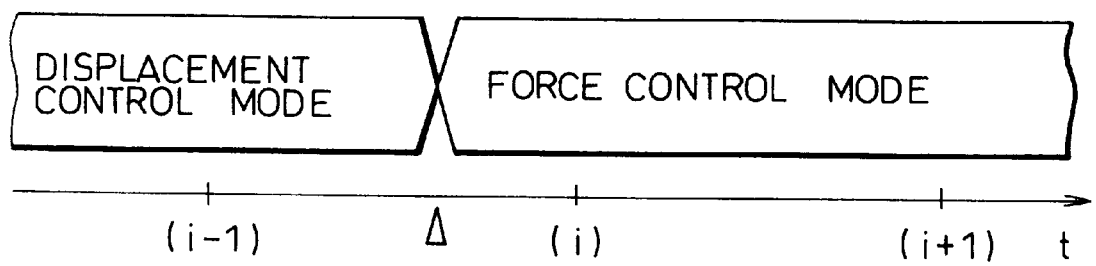
FIG. 25 is a conceptual view showing a changeover from a displacement control mode to a force control mode.

More specifically, the changeover of control mode is executed in response to a request for changeover shown by triangular marks in FIGS. 24 and 25. At this time, if the control output value given to the servo system 11 just before the changeover and that just after the changeover are equal to each other, no substantial change occurs in operational state of the servo system 11, so that the load applied to the test piece S does not change at the time of changeover of control mode.

More specifically, in the case of controlling the servo system 11 at intervals of a predetermined control cycle, the changeover of control system can be made without giving a shock to the test piece, if the control output value $U_K(i-1)$ given from the controller 17a of the force control system 12 at the control timing [i-1] just before the control system changeover is equal to the control output value $U_H(i)$ given from the controller 17b of the displacement control system 13 to the servo system 11 at the control timing [i] just after the control system changeover. Similarly, the changeover from the displacement control mode to the force control mode can be made without causing a shock, if the control output value $U_H(i-1)$ given from the controller 17b of the displacement control system 13 to the servo system 11 just before the mode changeover is equal to the control output value $U_K(i)$ given by the controller 17a of the force control system 12 to the servo system 11 just after the mode changeover.

In the present embodiment, the initial setting of a value of the integral term (the integral value $\Sigma K$ or $\Sigma H$ of error) for the post-changeover control system is carried out based on the control output value U(i-1) given to the servo system 11 at the control timing [i-1] just before the control system changeover, to eliminate the difference between the control output values $U_K$ and $U_H$, attributable to control gain difference, which would be otherwise observed just before and after the control system is changed over.

When a shift is made from the force control system 12 to the displacement control system 13, the control output value $U_K(i-1)$ at the control timing [i-1] in the force control system 12 is given by:

$$U_K(i-1) = P_K \cdot \Delta e_K(i-1) + I_K \cdot \Sigma K \quad (1a)$$

and the control output value $U_H(i)$ in the displacement control system 13 at the control timing [i] after the changeover is given by:

$$U_H(i)=P_H \cdot \Delta e_H(i)+I_H \cdot \Sigma H \qquad (2a).$$

Thus, the control output value $U_H(i)$ should be determined to satisfy the following relationship:

$$U_K(i-1)=U_H(i) \qquad (3).$$

The error $\Delta e_H(i)$ in the right side in formula (2a) can be determined in accordance with the displacement H(i) detected by the displacement gauge 6 and the target displacement $R_H(i)$ for the displacement control system 13, as shown by the following formula:

$$\Delta e_H(i)=R_H(i)-H(i).$$

From the view point of preventing a load variation at the time of control mode changeover, the target displacement $R_H(i)$ just after the mode changeover is preferably set to a value which is equal to the displacement H(i) which is in turn substantially the same, in general, to the actual displacement H(i−1) just before the mode changeover. The proportional control gain $P_H$ and the integral control gain $I_H$ are determined in dependence on the elastic constant of the test piece S. Thus, in respect of the control output value $U_H(i)$, no substantial discretion is given in arbitrarily setting the proportional term $P_H \cdot \Delta e_H(i)$ and the integral gain $I_H$. On the other hand, the integral value ΣH of error in the integral term $I_H \cdot \Sigma H$ in the right side of formula (2a) can be set arbitrarily. Therefore, the relationship shown in formula (3) can be satisfied by setting the integral value ΣH of error to an appropriate value in the initial setting.

In this regard, the integral value ΣH required to obtain the control output value $U_H(i)$ which is equal to the control output value $U_K(i-1)$ given to the servo system 11 at the control timing [i−1] just before the control mode changeover is calculated by the control system changeover means 14 in accordance with the following formula:

$$\Sigma H=(U_K(i-1)-P_H \cdot \Delta e_H(i))/I_H \qquad (4).$$

The control system changeover means 14 initially sets the thus calculated value as the integral value employed for control calculation which is shown in formula (2) and which is performed by the controller 17b. The integral value ΣH calculated in accordance with formula (4) based on the control output value $U_K(i-1)$ given to the servo system 11 just before the control mode changeover represents a history of the displacement of the test piece S caused by the force applied thereto.

If a shift from the force control mode to the displacement control mode is made after the initial setting of the control output value $U_H$ for the displacement control system 13 is done with use of the integral value ΣH, the control output values $U_K(i-1)$ and $U_H(i)$ before and after the control mode shift are made equal to each other, whereby the changeover between the control systems 12 and 13 can be made smoothly. That is, a difference between these control output values can be absorbed which difference would be otherwise caused due to the difference between the control gains for the control systems 12 and 13.

In a similar manner, a shift from the displacement control system 13 to the force control system 12 is carried out. That is, in order to satisfy formula (6) given below, i.e., to make the control output value $U_H(i-1)$, determined from equation (5a), in the displacement control system 13 at the control timing [i−1] equal to the control output value $U_K(i)$, determined from equation (5b), in the force control system 12 at the control timing [i], the integral value ΣK which is to be initially set for the force control system 12 is determined in accordance with formula (7):

$$U_H(i-1)=P_H \cdot \Delta e_H(i-1)+I_H \cdot \Sigma H \qquad (5a)$$

$$U_K(i)=P_K \cdot \Delta e_K(i)+I_K \cdot \Sigma K \qquad (5b)$$

$$U_H(i-1)=U_K(i) \qquad (6)$$

$$\Sigma K=(U_H(i-1)-P_K \cdot \Delta e_K(i))/I_K \qquad (7).$$

According to the material testing machine having the control system changeover means 14 which has the function of making the control output values $U_K$ and $U_H$, respectively supplied from the controller 17a of the force control system 12 and the controller 17b of the displacement control system 13 before and after the changeover of control system, equal from each other by the initial setting of the integral values ΣK and ΣH, extra work of temporarily terminating the operation of the servo system 11 to thereby reset the load applied to the test piece S to zero becomes unnecessary, whereby the changeover of control mode can be made easily, as needed. In addition, the changeover of control mode can be carried out in a condition that the control output value U supplied to the servo system 11 is kept unchanged, and therefore, an undesired shock never be applied to the test piece S.

The control mode changeover of the present embodiment may be modified variously.

For instance, by setting the error Δe supplied to post-changeover control system 12 or 13 to substantially zero, the mode changeover can be made with ease. That is, by setting the initial value of the target force or the target displacement just after the mode changeover to be equal to the actual force or the actual displacement detected just before the mode changeover, the error Δe just after the mode changeover can be set to a value of zero. By doing this, the control calculation upon mode changeover can be simplified.

The initial setting of integral value ΣH or ΣK may be made only if the control gain difference between the force control system and the displacement control system is large enough to produce a large change in the control output value at the time of mode changeover. More specifically, such initial setting may be made only if it is expected in an estimation based on the elastic constant of the test piece S that a change greater than a threshold value will occur in the control output value at the time of mode changeover. Further, the initial setting of integral value ΣH or ΣK may be selectively performed depending on whether or not the ratio between the target displacement in the displacement control system and the target displacement determined by conversion of the target force in the force control system to target displacement exceeds a threshold value.

The present invention is not limited to the foregoing embodiment, but may be modified variously. It is understood that the present invention may be modified without departing from the scope or spirit of the invention.

What is claimed is:

1. A material testing machine for measuring a mechanical property of a test piece based on a load given to the test piece and a mechanical change generated in the test piece, while feedback-controlling an operation of a servo system including a hydraulic actuator which gives the load to the test piece by means of a controller such that an actual load applied to the test piece coincides with a target load, comprising:

gain setting means for setting the control gain for the feedback control performed during material testing;

estimating means for estimating the mechanical property of the test piece based on the actual load and the mechanical change in the test piece which are periodically detected during the material testing performed while carrying out the feedback control;

gain correcting means for correcting the control gain set by said gain setting means in accordance with the estimated mechanical property; and wherein said gain correcting means corrects the control gain set by said gain setting means to coincide with the control gain which corresponds to the estimated mechanical property determined by said estimating means, by searching a table in which the control gain for every type of test piece is set in advance as a function of the mechanical property of the test piece.

2. A material testing machine for measuring a mechanical property of a test piece based on a load given to the test piece and a mechanical change generated in the test piece, while feedback-controlling an operation of a servo system including a hydraulic actuator which gives the load to the test piece by means of a controller such that an actual load applied to the test piece coincides with a target load, comprising:

load maintaining means for maintaining load observed at a time when a minute change in the test piece is detected while applying a gradually increasing load prior to material testing;

estimating means for estimating a mechanical property of the test piece based on the actual load and the mechanical change of the test piece respectively detected after a displacement of the test piece is stabilized while the load observed when the minute change in the test piece was detected is maintained;

initial gain setting means for setting an initial value of the control gain for the feedback control in accordance with the estimated mechanical property of the test piece;

wherein said initial setting means sets the control gain at a minimum value of the control gain when giving of the load to the test piece is started prior to material testing, and thereafter the control gain is gradually increased with elapse of time; and the minute change in the test piece is detected when a mechanical change in the test piece beyond detecting resolution of a detector is detected.

3. A material testing machine for measuring a mechanical property of a test piece based on a load given to the test piece and a mechanical change generated in the test piece, while feedback-controlling an operation of a servo system including a hydraulic actuator which gives the load to the test piece by means of a controller such that an actual load applied to the test piece coincides with a target load, comprising:

load maintaining means for maintaining load observed at a time when a minute change in the test piece is detected while applying a gradually increasing load prior to material testing;

estimating means for estimating a mechanical property of the test piece based on the actual load and the mechanical change of the test piece respectively detected after a displacement of the test piece is stabilized while the load observed when the minute change in the test piece was detected is maintained;

initial gain setting means for setting an initial value of the control gain for the feedback control in accordance with the estimated mechanical property of the test piece; and wherein said initial gain setting means searches a table in which the control gain is stored beforehand as a function of the mechanical property of the test piece, to thereby set the initial value of the control gain based on the mechanical property estimated by said estimating means.

4. A material testing machine for measuring a mechanical property of a test piece based on a load given to the test piece and a mechanical change generated in the test piece, while feedback-controlling an operation of a servo system including a hydraulic actuator which gives the load to the test piece by means of a controller such that actual load applied to the test piece coincides with target load, comprising:

a force control system including a controller for feedback-controlling the operation of the servo system based on an actual force applied to the test piece, the actual force serving as a controlled variable in the feedback control;

a displacement control system including a controller for feedback-controlling the operation of the servo system based on an actual displacement of the test piece, the actual displacement serving as a controlled variable in the feedback control; and control system changeover means for selectively operating either said force control system or said displacement control system, said control system changeover means making initial setting of a control output value to be supplied from the controller in the post-changeover control system, based on a control output value supplied from the controller in the pre-changeover control system to the servo system just before the changeover, and then making the control system changeover.

5. The material testing machine according to claim 4, wherein the controller of the force control system determines the control output value $U_K$ to be supplied to the servo system in accordance with a formula given by:

$$U_K = P_K \cdot \Delta e_K + I_K \cdot \Sigma K$$

where $P_K$ and $I_K$ represent a proportional control gain and an integral control gain which are set beforehand, and $\Delta e_K$ and $\Sigma K$ represent an error between a target force and an actual force applied to the test piece and an integral of the error;

the controller of the displacement control system determines the control output value $U_H$ to be supplied to the servo system in accordance with a formula given by:

$$U_H = P_H \cdot \Delta e_H + I_H \cdot \Sigma H$$

where $P_H$ and $I_H$ represent a proportional control gain and an integral control gain which are set beforehand, and $\Delta e_H$ and $\Sigma H$ represent an error between a target displacement and an actual displacement of the test piece and an integral of the error; and the control system changeover mean determines, based on the control output value $U_K$ or $U_H$ given to the servo system just before the control system changeover, the integral $\Sigma H$ or $\Sigma K$ of the error between the controlled variable initially set in the post-changeover control system and a control objective value in accordance with formulas, given by:

$$\Sigma H = (U_K - P_H \cdot \Delta e_H)/I_H$$

$$\Sigma K = (U_H - P_K \cdot \Delta e_K)/I_K$$

to thereby make the control output values $U_K$ and $U_H$ equal to each other, which values are given to the servo system before and after the control system changeover.

* * * * *